United States Patent [19]

Hofmann et al.

[11] Patent Number: 5,212,202
[45] Date of Patent: May 18, 1993

[54] THERAPEUTIC CHOLESTEROL GALLSTONE DISSOLUTION METHOD

[75] Inventors: Alan F. Hofmann; Claudio D. Schteingart, both of La Jolla, Calif.

[73] Assignee: The Regents of the University of California, Oakland, Calif.

[21] Appl. No.: 871,182

[22] Filed: Apr. 20, 1992

Related U.S. Application Data

[63] Continuation-in-part of Ser. No. 513,684, Apr. 24, 1990, abandoned, which is a continuation-in-part of Ser. No. 341,900, Apr. 24, 1989, abandoned.

[51] Int. Cl.$^5$ .................................................. A61K 31/22
[52] U.S. Cl. ........................................ 514/546; 514/877
[58] Field of Search ................................ 514/546, 877

[56] References Cited

U.S. PATENT DOCUMENTS

| | | | |
|---|---|---|---|
| 4,205,086 | 5/1980 | Babayan | 424/312 |
| 4,758,596 | 7/1988 | Thistle et al. | 514/722 |
| 4,902,276 | 2/1990 | Zakko | 604/28 |
| 4,910,223 | 3/1990 | Hofmann | 514/552 |

OTHER PUBLICATIONS

Takasawa et al., "A Study on the Dissolution . . . ", *Tohoku J. Exp. Med.*, 138, 383-395 (1982).
Leuschner et al., "Alternating Treatment . . . ", *Scand. J. Gastroent.*, 16, 497-503 (1981).
Leuschner et al., "Gallstone Dissolution . . . ", *Amer. J. Gastroent.*, 77, 4, 222-226 (1982).
Lueschner et al., "Biochemical and Morphological . . . ", *Amer. J. Gastroent.*, 79, 4, 291-298 (1984).
Motson, "Dissolution of Common . . . ", *Br. J. Surg.*, 68, 203-208 (1981).
Leuschner et al., "Investigations on the Toxicity . . . ", *Digestion*, 30, 23-32 (1984).
Carey et al., "Cholelithiasis and Cholecystitis", in Conn, ed., Current Therapy 1981, 364-366 (1981).
Allen et al., "Cholelitolysis Using . . . ", *Gastroenterology*, 88, 122-125 (1985).
Allen et al., "Rapid Dissolution . . . ", N. Eng. J. Med., 312, 4, 217-220 (1985).
Ponz de Leon et al., "The Effect of Dihydroxydibutylether . . . ", *Intl. J. Clin. Pharm., Ther. and Toxicol.*, 21, 1, 37-40 (1983).
Missale et al., "Effect of Dihydroxydibutylether . . . ", *Int. J. Clin.* Pharm. Ther. and Toxicol., 19, 6, 273-274 (1981).
Sama et al., "A Double-Blind Comparison . . . ", *Intl. J. Clin. Pharm., Ther. and Toxicol.*, 21, 2, 95-97 (1983).
Leuschner et al., "Dissolution of Bileduct Stones", *The Lancet*, 336 (Feb. 7, 1981).
Leuschner et al., "The Dissolution of CBD Cholesterol . . . ", *Gastroenterology*, 88, 5, 1674 (1985).
Leuschner et al., "Our 10 Years' Experience . . . ", *Gastroenterology*, 82, 5, 1113 (1982).
Allen et al., Abstract No. 44, "Methyl Tertiary Butyl Ether . . . " and Abstract No. 45, Gallstone Dissolution . . . , *Hepatology*, 3, 5, 809 (1983).
Bugliosi et al., "Rapid Gallstone Dissolution . . . " Gastroenterology, 86, 5, 1350 (1984).
Buliosi et al., "Methyl Tertiary-Butyl Ether (MTBE) . . . ", Gastroenterology, 86, 5, 1313 (1984).

*Primary Examiner*—Frederick E. Waddell
*Assistant Examiner*—Raymond J. Henley, III
*Attorney, Agent, or Firm*—Brown, Martin, Haller & McClain

[57] ABSTRACT

A method and apparatus are disclosed for treating a patient having cholesterol calculi which involves infusing into the biliary tract of said patient a $C_5$-$C_6$ ester having a boiling point in the range of 80°-140° C. in an amount and at a flow rate effective to at least partially dissolve said calculi rapidly. It is found that the ester has little or no tendency to accumulate in the blood stream when perfused into a patient, particular as compared to methyl t-butyl ether (MTBE), the solvent widely used at present. The invention also encompasses dissolving cholesterol calculi by exposing such calculi to contact with effective quantities of those solvent compounds. The method preferably uses a high flow rate catheter pumping system for infusing a gallstone dissolution solvent into the gallbladder of a patient and aspirating the gallstone dissolution solvent from the gallbladder, and a unit measure container of the solvent. The preferred esters are n-propyl acetate, isopropyl acetate, ethyl propionate and ethyl isobutyrate, with ethyl propionate being the most preferred. Contact flow rates are sufficiently high to insure fluid turbulence in the biliary tract region surrounding the calculi.

24 Claims, No Drawings

THERAPEUTIC CHOLESTEROL GALLSTONE DISSOLUTION METHOD

CROSS-REFERENCE TO RELATED APPLICATION

The application is a Continuation-in-part of U.S. patent application Ser. No. 07/513,684, filed Apr. 24, 1990, now abandoned which in turn is a continuation-in-part of U.S. patent application Ser. No. 07/341,900, filed Apr. 24, 1989.

BACKGROUND OF THE INVENTION

1. Field of the Invention:

The invention herein relates to medical treatments of cholesterol calculi (particularly gallstones) by contact dissolution with organic solvents. More particularly it relates to therapeutic methods using low viscosity non-toxic pumpable solvents.

2. Background of the Prior Art:

The contact dissolution of cholesterol gallstones by organic solvents in human patients is a well recognized medical procedure and may be favored over surgical procedures to remove gallstones in patients at increased risk of surgery; see, for instance, U.S. Pat. No. 4,205,086. The dissolution procedures normally involve infusion of the solvent into the biliary tract (including the gallbladder and the bile ducts) by means of a T-tube, nasobiliary tube, percutaneous transhepatic catheter or cholecystostomy tube by use of a constant infusion pump or by gravity or by manual repeated installation and withdrawal using a syringe; see Palmer, et al., *Gut*, 27, 2, 196 (1986). Often the stones fragment during the dissolution procedure, which advantageously increases the rate of dissolution.

A number of different types of solvents have been used or suggested for the dissolution procedure. These include organic solvents such as diethyl ether, chloroform or d-limonene as well as aqueous micellar solutions of bile salts. The aforementioned U.S. Pat. No. 4,205,086 also lists a large number of useful liquid fatty acids and the alcohol esters thereof. A further solvent which has received substantial attention is monooctanoin, mentioned in U.S. Pat. No. 4,755,167 and several articles, such as Thistle, et al., Gastroenterology 78, 5, 1016 (1980). More recently a $C_5$ ether, methyl t-butyl ether (MTBE) has been used as a cholesterol gallstone solvent; see, e.g., Allen, et al., *Gastroenterology*, 88, 1, 122 (1985); Thistle, et al., U.S. Pat. No. 4,758,596; and Thistle, et al., *N. Engl. J. Med.*, 320, 633 (1989).

While all of these materials have shown some efficacy in in vivo and/or in vitro tests, all have some undesirable side effects or physical properties. Monooctanoin, for instance, has a relatively high viscosity and dissolves gallstones very slowly. MTBE was selected by Thistle,, et al., because its boiling point is above body temperature, and is currently the solvent most often considered to have the best potential for contact cholesterol gallstone dissolution. However, it is known to have definite side effects, including nausea and vomiting, which it is believed are caused by increased levels of MTBE in the blood; see Esch et al., *Gastroenterology*, 100, 4315 (1991). Further, if MTBE escapes from the gallbladder into the small intestine, it causes signs of systemic toxicity (sedation), pain and by endoscopy, damage to the epithelium of the small intestine. Entry of MTBE into the blood stream causes hemolysis, and one case of renal failure (reversible) has been reported. MTBE also has a relatively low boiling point (55° C.), not far above ordinary body temperature, which poses some volatility problems in use because of its low flash point and strong, unpleasant odor. Those materials such as diethyl ether which have boiling points below body temperature are hazardous for clinical use because of rapid volatilization and marked increase in volume in use.

While as noted prior art has generally indicated that cholesterol gallstones can be dissolved using esters in the $C_2$-$C_{20}$ range [see the aforesaid U.S. Pat. No. 4,205,086 and Flynn et al., *J. Pharm. Sci.*, 68, 9, 1090 (1979)], such treatments as described were taught to be unduly slow, requiring on the order of several days. It is normally unacceptable to perfuse a patient for such an extended period; not only is the risk to the patient high for a prolonged period, but in addition it is likely that the patient's normal movements during that time, even though restricted, may be sufficient to impair the perfusion. Neither of these references has taught any focus on the $C_5$-$C_6$ esters are being free of problems such as slow dissolution rates or concentration of solvent in the blood stream.

Recently there has been developed a novel infusion pump which produces a high flow rate at low pressure. This pump has been described and claimed in U.S. Pat. No. 4,902,276, issued Feb. 20, 1990, and U.S. patent application Ser. No. 07/482,194 (Feb. 20, 1990) by S. Zakko (the "Zakko pump"). While this pump has proved very affective for gallstone dissolution, its satisfactory performance depends on being used with relatively low viscosity solvents.

It would therefore be advantageous to have a therapeutic procedure available in which cholesterol gallstones could be easily, safely and rapidly dissolved by a solvent which would be effective for dissolution of cholesterol gallstones, free of a tendency to accumulate in the blood stream, easy and safe to handle for medical personnel and capable of being used in the most effective equipment such as the Zakko pump.

BRIEF SUMMARY OF THE INVENTION

We have now unexpectedly and surprisingly discovered that certain $C_5$-$C_6$ esters, notably ethyl propionate (the ethyl ester of propionic acid), act extremely rapidly (within hours rather than days) to dissolve cholesterol gallstones, and do so without accumulating in the blood stream. Consequently, our invention may be described as follows:

In one aspect, the invention herein is a method for treating a patient having cholesterol calculi, particularly gallstones, which comprises infusing into the biliary tract of the patient a $C_5$-$C_6$ ester having a boiling point in the range of 80°–40° C. in an amount and at a flow rate effective to at least partially dissolve said calculi rapidly.

In another aspect, the invention herein is a method for dissolving cholesterol calculi (particularly gallstones) which comprises contacting said calculi with a $C_5$-$C_6$ ester having a boiling point in the range of 80°–40° C. in an amount and at a flow rate effective to at least partially dissolve said calculi rapidly.

In either aspect, it is found that the ester exhibits reduced (or no substantial) tendency to accumulate in the blood stream when perfused into the patient, as compared to the use of methyl t-butyl ether as a perfusion solvent.

The method may also be used to eliminate fragments of cholesterol gallstones, such as would be produced by fragmentation procedures (e.g., basketing, extracorporeal shockwave lithotripsy, and intracavital electrohydraulic lithotripsy).

Preferred among the $C_5$-$C_6$ esters are those selected from the group consisting of n-propyl acetate, isopropyl acetate, ethyl propionate and ethyl isobutyrate, more preferably ethyl propionate. These have all been found to produce rapid dissolution of cholesterol gallstones (at a rate generally comparable to that of MTBE) without problems of volatility, excessive viscosity or accumulation in the blood stream.

DETAILED DESCRIPTION AND PREFERRED EMBODIMENTS

The efficacy of the methods of this invention can be best understood by consideration of the characteristics of cholesterol calculi and the specific $C_5$-$C_6$ ester solvents useful in the invention.

As used herein, the term "cholesterol calculi" means those concretions which generally develop in the biliary tract within humans and animals and which contain at least about 40% cholesterol. Well known common cholesterol calculi are cholesterol biliary duct stones and gallstones. Within the biliary tract, such stones may occur in the hepatic ducts, bile ducts, gallbladder or sphincter of Oddi. Also, the term "biliary tract" will be recognized to encompass both the gallbladder and the bile ducts.

Consideration of the usual equations used to describe dissolution of a sphere by a fluid under turbulent conditions indicates that not only equilibrium solubility but also viscosity is important. This is because viscosity influences the diffusion of cholesterol in the unstirred layer immediately surrounding the stone (according to the Stokes-Einstein relationship). In addition, low viscosity is important since catheters used for this purpose must have a small bore (usually less than 8 French), with a high flow—low pressure pumping system such as that of the Zakko Pump. The pressure needed to obtain a given flow varies inversely as the 4th power of the radius, and directly with the viscosity of the fluid being pumped. Thus for a small bore tube, the lower the viscosity, the greater is the solvent flow for a given pressure.

There are additional requirements for a satisfactory solvent. It must be relatively non-toxic in several aspects. First, the solvent must not damage the gallbladder mucosa significantly during a several hour exposure of the mucosa to the anhydrous solvent. Second, the solvent must not damage the mucosa of the biliary duct system or the small intestine if the solvent leaks out of the gallbladder. The solvent should have little tendency to accumulate in the blood stream, but if any does so, it should cause little hemolysis when mixed with blood and should not cause release of toxic cytokines such as platelet activating factor. Further, it should not be toxic if it escapes into the peritoneal cavity. In addition, the solvent should have a pleasant odor so that if absorbed it does not induce nausea. Further, the solvent should be rapidly metabolized by digestive enzymes if it escapes into the gastrointestinal tract, and the resultant digestive products should be known to be safe.

Lastly, there are safety considerations in handling the solvent. If spilled, it should not cause danger to exposed employees. It should be a non-explosive and have a relatively high flash point. It should have a stable shelf life and not form peroxides or other explosive by-products.

Viscosity is known to vary directly with the number of molecular carbon atoms. It varies inversely approximately exponentially with temperature. Boiling point and flash point also vary directly with the total number of carbon atoms, but the relationship is not that simple. Cholesterol solubility in solvents can be correlated to some extent with solubility parameter considerations.

The determination of solvents suitable for effective contact dissolution of cholesterol gallstones thus involves multiple considerations. In addition, there are solute considerations. Cholesterol gallstones are composed of cholesterol monohydrate (and other insoluble salts); see Whiting, et al., *Clin. Sci.*, 68, 589 (1985). If gallstones are stored in the dry state, the water may evaporate so that the cholesterol monohydrate becomes anhydrous cholesterol. Therefore testing of solvents is best done on freshly harvested human gallstones which have been kept wet.

Based on these considerations, our research has led to the discovery that, while most esters cannot satisfy all (or in many cases, very many) of these criteria, one small group unexpectedly and surprisingly does substantially meet these criteria and therefore are highly effective, rapid action and safe solvents for the dissolution of cholesterol gallstones. These esters are limited to the class of those esters having 5-6 carbon atoms per molecule and with a boiling point in the range of 80°-140° C. These esters may be used alone or in admixture with each other. We have also discovered that within this class those compounds which are particularly preferred solvents, due to their most closely meeting the desirable criteria discussed above, are n-propyl acetate, isopropyl acetate, ethyl propionate and ethyl isobutyrate, with the most preferred being ethyl propionate. All of these are known compounds and need not be defined further here; their physical and chemical properties are well described in the literature.

Their efficacy and the techniques of the present invention may be seen from the following data. In the tests described in Table I below, fresh human faceted cholesterol gallstones (kept in distilled water) were dissolved in vitro and the times were recorded for the total dissolution, using a model gallbladder at a high flow rate achieved by a metering pump. "High flow rate" as used herein will mean rates of flow in the range which can be anticipated to result in fluid turbulence for the solvent in the region of the biliary tract surrounding the calculi (gallstones). While "high" rates will vary according to solvent type and viscosity and with individual patients, it will be expected that appropriate flow rates will be at least about 20 ml/min, preferably at least about 100 ml/min, and more preferably at least about 150 ml/min. For comparison purposes a parallel test with MTBE is also shown. The second column shows the weight of stone treated, of which 90% by weight can be considered to be cholesterol.

TABLE I

| Solvent | Boiling Point, °C. | Stone Weight, mg | Dissolution Time, min. | Rate, mg/min. |
|---|---|---|---|---|
| n-propyl acetate | 102 | 150 | 10 | 14 |
| isopropyl acetate | 89 | 147 | 14 | 9 |
| ethyl propionate | 99 | 140 | 10 | 13 |
| ethyl isobutyrate | 112 | 132 | 15 | 8 |
| methyl t-butyl ether | 55 | 175 | 8 | 20 |

It will be evident from these data that the $C_5$–$C_6$ ester solvents of this invention are essentially similar to the known MTBE in their ability to rapidly dissolve cholesterol gallstones, while yet having substantially higher boiling points than MTBE and thus substantially less potential for problems with volatility. It will also be evident that ethyl propionate is overall the most satisfactory of the esters.

Toxicological considerations indicate that the named solvents have a low order of toxicity.

In another series of experiments, the effectiveness of propyl acetate, isopropyl acetate, ethyl propionate and ethyl isobutyrate esters versus MTBE in dissolving cholesterol gallstones was determined in vitro. For this study stones from five cholecystectomy patients were matched. All stones were visually judged to be primarily cholesterol. The mean stone weight for the test sets (five stones each) ranged from 79–340 mg. The test protocol utilized a 30 ml polyethylene bag as a model gallbladder. One stone was dissolved at a time. For each stone a reservoir containing 150 ml of solvent was used. Flow to the bag was maintained at 180 ml/min. A closed loop pumping system was employed to deliver the solvent to the experimental stone within the polyethylene bag. A Medical Disposables International subclavian catheter (#1900115A) was used to deliver and withdraw the solvent and monitor pressure which controlled the pump. This catheter consisted of two 18 gage lumens and a single 16 gage lumen. The larger lumens were used to aspirate and infuse the solvent and the smaller lumen was used to monitor pressure within the model gallbladder. The termination of each lumen was a single port. Feed back from the pressure transducer was used to control the pumps to delivery 180 ml/min within a predetermined intralumen pressure. A flow of 180 ml/min was used to assure high turbulence and obtain optimum dissolution rates due to high rates of mass transfer. Complete dissolution was defined as the disappearance of all debris in the model gallbladder. The data are summarized in Table II.

TABLE II

|  | Mean Time, min. | Overall Rate, mg/min. |
|---|---|---|
| ethyl propionate | 14 | 12.22 |
| isopropyl acetate | 26 | 5.48 |
| ethyl isobutyrate | 33 | 4.55 |
| propyl acetate | 35 | 4.45 |
| Methyl t-butyl ether | 19 | 7.69 |

This comparison shows the esters tested to be substantially equivalent to MTBE. The variation in rates is well within experimental expectations, since great differences exist from stone to stone for each solvent and the surface area per unit volume increases as the stone diameter (weight) decreases for similar materials and for similar geometries. It is also expected that the chemical differences from stone to stone may cause one solvent to perform appreciably different than the next. It also illustrates again the particular efficacy of ethyl propionate.

Metabolic considerations indicate that the esters (n-propyl acetate, isopropyl acetate, ethyl propionate and ethyl isobutyrate) are likely to be hydrolyzed by digestive esterases and quickly converted to the corresponding alkanol and aliphatic acid (which will ionize). The hydrolysis products—ethanol, n-propanol and isopropanol and the acetate, propionate and butyrate ions—all have a low degree of toxicity. We also anticipate that a mixture of the solvents may have less toxicity (expressed per unit volume of solvent) than any of the solvents alone because each of the solvents undergoes a different metabolic pathway.

A third series of experiments also illustrates a surprising and important property of the esters useful in this invention, the ability to be rapidly hydrolyzed (and/or removed from the blood stream by tissues) and avoid accumulation in the blood stream. Ethyl propionate and MTBE (10 ml) were perfused in separate experiments into and out of the gallbladder of an anesthetized pig for a period of two hours, using apparatus similar to the Zakko pump described above. Blood samples were taken using gas-tight syringes from a central vein before, at one hour and at two hours of perfusion, and at thirty and sixty minutes following perfusion, and analyzed for ethyl propionate or MTBE by gas chromatography using a flame ionization detector. It was found that during MTBE perfusion blood levels of MTBE rose to 0.01–0.1 $\mu l/$ ml (84–840 $\mu$mole/l) and declined after perfusion. In contrast, however, ethyl propionate levels remained below the level of detectability at all times throughout the procedure. It is to be expected that at such extremely low levels in the blood, use of the esters of this invention will substantially reduce or eliminate most of the patient side effects seen in the conventional MTBE solvent usage.

Any suitable technique of infusion of the described solvents into a patient in the method of this invention can be used; normally the one chosen will be as that described in the prior art for other solvents, including monooctanoin and MTBE. The solvents are normally used in undiluted liquid form, but if desired may also be used as part of mixtures with inert liquid carriers. Since dissolution is a contact phenomenon it will be recognized that dilution in such mixtures will normally slow the rate of dissolution and extend the time needed to achieve the desired degree of gallstone dissolution. The compounds can also be equilibrated with water, saline or other aqueous solutions to avoid tissue dehydration.

Another aspect of the invention is the in vivo dissolution of gallstones using the $C_5$–$C_6$ ester solvents provided herein as the solvent in a high flow rate pumping system, in particular a continuous pumping system controlled by gallbladder pressure feedback and employing a delivery system consisting of a catheter, a continuous flow pumping system, a controller and a tubing set; see aforesaid U.S. patent application No. 07/482,194, filed Feb. 20, 1990, to S. Zakko, incorporated herein by reference.

In general, the system shown in that application is capable of operating continuously at a high flow rate to produce continuous turbulence in the gallbladder while assuring that the intra-luminal gallbladder pressure does not exceed the critical leakage pressure, thereby preventing solvent from entering the intestine through the cystic and common bile ducts. Such a pumping system, in combination with the low viscosity solvent provided herein, has the capability of emptying the gallbladder many times faster than the rate of normal gallbladder contraction, to prevent solvent from emptying into the intestine should such a gallbladder contraction occur during perfusion. The system is however designed to permit internal pressure transients due to patient coughing, laughing, movement and the like without interrupting the solvent flow.

The system will accept flow calibrations of both infusion and aspiration pumps and operate those pumps at substantially equal flow rates to minimize the control modulation and maximize the overall flow rate. The controller of the system can, for example, accept, upon command, flow rate, set pressure, lower pressure limit, upper pressure limit and alarm conditions and permit the operation at flow rates of the solvent from close to zero to 250 ml/min, with normal perfusion occurring at flow rates preferably above about 150 ml/min. As previously mentioned, the present solvents, due to their low viscosities, are intrinsically efficient in contact dissolution due to enhanced mass transfer performance; furthermore, the high flow rates and attendant turbulence permitted by the low viscosity will enhance the dissolution effect.

The pump infuses solvent into the gallbladder of the patient through a catheter, which is constructed to permit the aspiration and infusion of the disclosed low viscosity class of esters at flow rates up to 250 ml/min while requiring no more than an 8 french catheter size. Such a catheter includes an infusion lumen, an aspiration lumen and a pressure sensing lumen to permit the continuous remote monitoring of intra-gallbladder pressure with a column of physiological saline. The catheter also includes a retention device to secure the catheter within the gallbladder intra- and post- operatively.

The catheter is supplied with solvent by a tubing set and reservoir which may be provided as a disposable kit. The tubing, catheter and reservoir are constructed of materials compatible with the selected solvent. The tubing must be strong enough to be used in a peristaltic pump in which solvent is being infused or aspirated at flow rates up to 250 ml/min. and yet not limit flow or permit elastic deformation under positive or negative pressure which would adversely reduce the frequency response of the pump to control gallbladder pressure. Additionally, the reservoir allows for the gravity separation of bile and solvent, thereby permitting aspirated solvent to be reinfused.

Preferably a microprocessor responsive to system pressure operates an infusion pump at the desired flow rate. The aspiration pump is driven at varying speeds when the pressure is above or below the desired pressure, and at a constant speed when the pressure is in the vicinity of the desired pressure, to keep the gallbladder pressure within the upper and lower pressure limits.

Further, should the pressure remain above (as may occur with the beginning of a gallbladder contraction) or below the upper and lower pressure limits in excess of empirically determined delays, or above or below the upper and lower pressure alarms, for the associated delays, the controller causes the system to enter into an alarm mode in which both pumps operate in the aspiration direction at maximum flow rate to remove the low viscosity solvent.

The above procedure and equipment have been used with ethyl propionate as a solvent for the successful treatment of a human patient to eliminate cholesterol gallstones. In addition, it was found that the cholesterol concentrations observed in the solvent during the procedure were higher than concentrations observed during previous procedures conducted using MTBE, thus indicating more efficient cholesterol gallstone dissolution.

It will be understood by those skilled in the art that there are numerous other embodiments which are not described above but which are clearly within the scope and spirit of the invention. The description above is therefore intended to be exemplary only and the scope of the invention is to be limited solely by the appended claims.

We claim:

1. A method for dissolving cholesterol calculi which comprises contacting said calculi with a solvent comprising a $C_5$–$C_6$ ester having a boiling point in the range of 80°–40° C. in an amount and at a flow rate effective to dissolve said calculi at a dissolution rate of at least about 4 mg/min.

2. A method as in claim 1 wherein said ester is n-propyl acetate, isopropyl acetate, ethyl propionate or ethyl isobutyrate.

3. A method as in claim 2 wherein said ester is ethyl propionate.

4. A method as in claim 1 wherein said solvent is used in an undiluted form.

5. A method as in claim 1 wherein said solvent is equilibrated with an aqueous liquid.

6. A method as in claim 5 wherein said aqueous liquid is water, saline or an aqueous solution.

7. A method as in claim 1 wherein said solvent is used in a form in which it is mixed with and diluted by an inert carrier liquid.

8. A method as in claim 1 wherein said contacting comprises pumping said solvent past said calculi.

9. A method as in claim 8 wherein said pumping is conducted at a high solvent flow rate.

10. A method as in claim 9 wherein said pumping is conducted at a high solvent flow rate at low pressure.

11. A method as in claim 9 wherein said high solvent flow rate is on the order of at least 20 ml/min.

12. A method as in claim 11 wherein said high solvent flow rate is on the order of at least 100 ml/min.

13. A method as in claim 12 wherein said high solvent flow rate is on the order of at least 150 ml/min.

14. A method as in claim 1 wherein the rate of dissolution of said calculi is on the order of at least 8 mg/min.

15. A method as in claim 14 wherein the rate of dissolution of said calculi is on the order of 8–14 mg/min.

16. A method for treating a patient having cholesterol calculi in the biliary tract which comprises perfusing into the biliary tract of said patient a solvent comprising a $C_5$–$C_6$ ester having a boiling point in the range of 80°–140° C. in an amount and at a flow rate effective to dissolve said calculi at a dissolution rate of at least about 4 mg/min.

17. A method as in claim 16 wherein said ester is n-propyl acetate, isopropyl acetate, ethyl propionate or ethyl isobutyrate.

18. A method as in claim 17 wherein said ester is ethyl propionate.

19. A method as in claim 16 wherein said infusion comprises pumping said solvent through said patient's biliary tract.

20. A method of gallstone dissolution using a high flow rate catheter pumping system for infusing a gallstone dissolution solvent into the gallbladder of a patient, and aspirating the gallstone dissolution solvent from the gallbladder characterized in which the solvent comprises a $C_5$–$C_6$ ester having a boiling point in the range of 80°–40° C. in an amount characterized in that said infusing and aspirating is at a flow rate effective to dissolve said calculi at a dissolution rate of at least about 4 mg/min.

21. A method as is claim 20 wherein said flow is continuous and at a rate sufficient to cause sustained turbulence within the gallbladder.

22. A method as in claim 20 wherein said solvent is infused at a rate about 150 ml/min.

23. A method as in claim 20 wherein said ester is n-propyl acetate, isopropyl acetate, ethyl propionate or ethyl isobutyrate.

24. A method as in claim 23 wherein said ester is ethyl propionate.

* * * * *

UNITED STATES PATENT AND TRADEMARK OFFICE
CERTIFICATE OF CORRECTION

PATENT NO. : 5,212,202
DATED : May 18, 1993
INVENTOR(S) : Alan F. Hofmann, et al.

It is certified that error appears in the above-identified patent and that said Letters Patent is hereby corrected as shown below:

Column 2, line 53 "80°-40°C." should be --80°-140°C.--

Column 2, line 60 "80°-40°C." should be --80°-140°C.--

Column 8, Claim 1, line 9 "80°-40°C." should be --80°-140°C.--

Column 8, claim 20, line 65 "80°-40°C." should be --80°-140°C.--

Signed and Sealed this

Seventh Day of June, 1994

BRUCE LEHMAN

Attest:

Attesting Officer

Commissioner of Patents and Trademarks